US00RE48392E

(19) United States
(12) Reissued Patent
Hu

(10) Patent Number: US RE48,392 E
(45) Date of Reissued Patent: *Jan. 12, 2021

(54) CYCLIC PROCESS FOR THE PRODUCTION OF TAURINE FROM ALKALI ISETHIONATE

(71) Applicant: VITAWORKS IP, LLC, North Brunswick, NJ (US)

(72) Inventor: Songzhou Hu, Princeton, NJ (US)

(73) Assignee: Vitaworks IP, LLC, North Brunswick, NJ (US)

( * ) Notice: This patent is subject to a terminal disclaimer.

(21) Appl. No.: 16/863,384

(22) Filed: Apr. 30, 2020

Related U.S. Patent Documents

Reissue of:
(64) Patent No.: 9,428,451
Issued: Aug. 30, 2016
Appl. No.: 14/120,651
Filed: Jun. 12, 2014

U.S. Applications:
(63) Continuation-in-part of application No. 14/120,046, filed on Apr. 18, 2014, now Pat. No. 9,428,450.

(51) Int. Cl.
*C07C 303/32* (2006.01)
*C07C 303/02* (2006.01)
*C07C 303/44* (2006.01)

(52) U.S. Cl.
CPC ..... *C07C 303/32* (2013.01); *C07C 303/02* (2013.01); *C07C 303/44* (2013.01)

(58) Field of Classification Search
CPC .... C07C 303/32; C07C 303/02; C07C 303/44
See application file for complete search history.

(56) References Cited

U.S. PATENT DOCUMENTS

| | | | |
|---|---|---|---|
| 1,932,907 | A | 10/1933 | Nicodemus |
| 1,999,614 | A | 4/1935 | Nicodemus |
| 2,109,401 | A | 2/1938 | Nicodemus |
| 2,693,488 | A | 11/1954 | Sexton |
| 2,820,818 | A | 1/1958 | Sexton |
| 8,609,890 | B1 | 12/2013 | Hu |
| 9,061,976 | B1 | 6/2015 | Hu |

(Continued)

FOREIGN PATENT DOCUMENTS

| | | |
|---|---|---|
| CN | 101486669 | 7/2009 |
| CN | 101486669 A | 7/2009 |

(Continued)

OTHER PUBLICATIONS

Petition for inter partes review of U.S. Pat. No. 9,428,451 (IPR2018-01767), filed Sep. 28, 2018.

(Continued)

*Primary Examiner* — Alan D Diamond
(74) *Attorney, Agent, or Firm* — Myers Wolin, LLC

(57) ABSTRACT

A cyclic process is disclosed for the production of taurine from alkali isethionate in a high overall yield by continuously converting the byproducts of the ammonolysis reaction, sodium ditaurinate and sodium tritaurinate, to sodium taurinate. Sodium sulfate and residual taurine in the crystallization mother liquor are efficiently separated by converting taurine into a highly soluble form of sodium taurinate or ammonium taurinate while selectively crystallizing sodium sulfate.

7 Claims, 2 Drawing Sheets

(56) References Cited

U.S. PATENT DOCUMENTS

| | | | | |
|---|---|---|---|---|
| 9,108,907 | B1 | 8/2015 | Hu | |
| 9,428,450 | B2 | 8/2016 | Hu | |
| 9,428,451 | B2 | 8/2016 | Hu | |
| 9,573,890 | B2 | 2/2017 | Hu | |
| 9,593,076 | B2 | 3/2017 | Hu | |
| 9,598,357 | B1 | 3/2017 | Hu | |
| 9,598,360 | B2 | 3/2017 | Hu | |
| 9,745,258 | B1 | 8/2017 | Hu | |
| 9,815,778 | B1 | 11/2017 | Hu | |
| 9,850,200 | B1 | 12/2017 | Hu | |
| 9,926,265 | B1 | 3/2018 | Hu | |
| 9,994,517 | B1 | 6/2018 | Hu | |
| 10,040,755 | B2 | 8/2018 | Hu | |
| 10,071,955 | B1 | 9/2018 | Chen et al. | |
| 10,112,894 | B2 | 10/2018 | Hu | |
| 10,131,621 | B2 | 11/2018 | Hu | |
| 2014/0121405 | A1* | 5/2014 | Chen | C07C 303/18 562/104 |
| 2015/0210633 | A1 | 7/2015 | Hu | |
| 2015/0299113 | A1 | 10/2015 | Hu | |
| 2016/0340300 | A1 | 11/2016 | Hu | |
| 2016/0355470 | A1 | 12/2016 | Hu | |
| 2018/0093946 | A1 | 4/2018 | Hu | |
| 2018/0141899 | A1 | 5/2018 | Hu | |
| 2018/0155278 | A1 | 6/2018 | Hu | |
| 2018/0162806 | A1 | 6/2018 | Hu | |
| 2018/0312464 | A1 | 11/2018 | Hu | |
| 2019/0112260 | A1 | 4/2019 | Hu | |
| 2019/0112261 | A1 | 4/2019 | Hu | |
| 2019/0112262 | A1 | 4/2019 | Hu | |
| 2019/0135739 | A1 | 5/2019 | Hu | |

FOREIGN PATENT DOCUMENTS

| | | | |
|---|---|---|---|
| CN | 101508657 | | 8/2009 |
| CN | 101508657 | A | 8/2009 |
| CN | 101508658 | | 8/2009 |
| CN | 101508658 | A | 8/2009 |
| CN | 101508659 | | 8/2009 |
| CN | 101508659 | A | 8/2009 |
| CN | 101717353 | A | 6/2010 |
| CN | 104945289 | A | 9/2015 |
| CN | 105693559 | A | 6/2016 |
| CN | 105732440 | A | 7/2016 |
| CN | 106008280 | A | 10/2016 |
| CN | 107056659 | A | 8/2017 |
| DE | 219 023 | | 2/1985 |
| DE | 219023 | A3 | 2/1985 |
| WO | 0177071 | | 1/2001 |
| WO | WO 01/77071 | A1 | 10/2001 |

OTHER PUBLICATIONS

Decision instituting inter partes review of U.S. Pat. No. 9,428,451 (IPR2018-01767), dated Apr. 10, 2019.

Judgment in inter parties review of U.S. Pat. No. 9,428,451 (IPR2018-01767) and U.S. Pat. No. 9,573,890 (IPR2018-01768), dated Jul. 18, 2019.

Final Written Decision in inter partes review of U.S. Pat. No. 9,428,450 (IPR2018-01766), dated Apr. 2, 2020.

Excerpts of File History of U.S. Appl. No. 14/120,651, which issued as U.S. Pat. No. 9,428,451, issued Aug. 30, 2016.

Fuming Liu, "Process Design of Taurine Ammonolysis," China Chemical Trade, No. 8: 120 (Aug. 2013).

Jiang Wu & Zailin Guan, "Optimization on Ammonolysis in Manufacturing Method of Taurine", Journal of Hubei Polytechnic University, 19(1): 23-26 (Feb. 2004).

O.M. Bondareva et al., "Synthesis of Taurine," 42 J. Pharm. Chem. 142 (2008).

Jie Yang et al., "Improved Technology for Synthesis of Taurine," Chemical Industry and Engineering Progress, 24(11):1269-72 (2005).

Robert E. Maleczka's 2nd Declaration in Support of Patent Owner's Response for Inter Partes Review of U.S. Pat. No. 9,428,450, IPR2018-01766, dated Jul. 12, 2019, 81 pages, Vitaworks Exhibit 2007.

Petitioner's Reply to Patent Owner's Response for Inter Partes Review of U.S. Pat. No. 9,428,450, IPR2018-01766, dated Oct. 7, 2019, 38 pages.

Declaration of Mark A. Lipton in Support of Peitioner's Reply to Patent Owner's Response dated Oct. 7, 2019, 33 pages.

Declaration of Joe P. Foley, Ph.D. in Support of Peitioner's Reply to Patent Owner's Response, dated Oct. 7, 2019, 34 pages.

Patent Owner's Surreply for Inter Partes Review of U.S. Pat. No. 9,428,450, IPR2018-01766, dated Nov. 15, 2019, 33 pages.

Final Written Decision for Inter Partes Review of U.S. Pat. No. 9,428,450, IPR2018-01766, dated Apr. 2, 2020, 65 pages.

Objective Indicia Exhibit A: Excerpt from "Bulletin of Ministry of Environment Protection of China", Jan. 27, 2015, with English summary, and excerpt from "Environment Impact Assessment Report of 25,000/Year Taurine Plant of Hubei Grand Life Science and Technology Co. Ltd.", dated Jul. 24, 2017, with English summary.

Objective Indicia Exhibit B: "Production Flowchart of Taurine in Environmental Impact Assessment Report of Jiangying Huachang Food Additive Company", 2005, with English translation of flowchart.

Objective Indicia Exhibit C: "Production Flowchart of Taurine in Amended Environmental Impact Assessment Report of Jiangying Huachang Food Additive Company", 2017, with English translation of flowchart.

Objective Indicia Exhibit D: Selected Pages from Qiangjiang Yongan Pharmaceutical Co. Annual Reports 2012-2015, with partial English translations.

Objective Indicia Exhibit G: "Study of the Ammonolysis Reaction for Taurine" Liu 2015; Liu Fuming & Xie Liming, Shandong Chemical Industry, May 2015, vol. 44, No. 5, pp. 27-28, 30, with English translations.

Objective Indicia Exhibit H: Liu 2013, Liu Fuming, China Chemical Trade Monthly Journal, Aug. 2013, vol. 5, Issue. 8, HGL Exhibit 1019.

Objective Indicia Exhibit I: Wu 2004, Wu Jiang & Guan Zailin J. , Journal of Hubei Polytechnic University, Feb. 2004, vol. 19, No. 1, pp. 23-26, HGL Exhibit 1016.

Office Action issued by the Canadian Intellectual Property Office for corresponding Canadian Patent Application No. 2,946,181, dated Mar. 26, 2018.

Notification of Reasons for Rejection issued by the Japan Patent Office for corresponding Japanese Patent Application No. 2017-505693, dated Mar. 27, 2018, with an English translation.

Extended European Search Report issued by the European Patent Office for corresponding European Patent Application No. EP18154790.2, dated Jun. 25, 2018.

USPTO Non-Final Office Action for corresponding U.S. Appl. No. 15/870,844 dated May 10, 2018.

USPTO Notice of Allowance for corresponding U.S. Appl. No. 15/870,844 dated Jun. 15, 2018.

Curriculum Vitae (CV) of Robert E. Maleczka, as of Jul. 12, 2019, 39 pages, Vitaworks Exhibit 2008.

Objective Indicia filed with Response dated Jul. 25, 2019, 11 pages. Results for experiments conducted between May 14, 2019 and Jun. 30, 2019, Vitaworks Exhibits 2009-2065.

Notice of Allowance issued by the United States Patent and Trademark Office for corresponding U.S. Appl. No. 14/120,046, dated May 24, 2016.

Notice of Allowance issued by the United States Patent and Trademark Office for corresponding U.S. Appl. No. 14/120,046, dated Jul. 14, 2016.

Notice of Allowance issued by the United States Patent and Trademark Office for corresponding U.S. Appl. No. 15/238,621, dated Oct. 5, 2016.

Non-Final Office Action issued by the United States Patent and Trademark Office for corresponding U.S. Appl. No. 15/228,539, dated Oct. 17, 2016.

Final Office Action issued by the United States Patent and Trademark Office for corresponding U.S. Appl. No. 14/120,046, dated Dec. 8, 2015.

(56) References Cited

OTHER PUBLICATIONS

Notice of Allowance issued by the United States Patent and Trademark Office for corresponding U.S. Appl. No. 15/228,539, dated Dec. 23, 2016.
Notice of Allowance issued by the United States Patent and Trademark Office for corresponding U.S. Appl. No. 15/238,621, dated Jan. 4, 2017.
Notice of Allowance issued by the United States Patent and Trademark Office for corresponding U.S. Appl. No. 15/228,568, dated Jan. 17, 2017.
Notice of Allowance issued by the United States Patent and Trademark Office for corresponding U.S. Appl. No. 14/120,651, dated Aug. 2, 2016.
Non-Final Office Action issued by the United States Patent and Trademark Office for corresponding U.S. Appl. No. 16/030,605, dated Aug. 9, 2018.
Final Office Action issued by the United States Patent and Trademark Office for corresponding U.S. Appl. No. 16/030,605, dated Jan. 30, 2019.
Non-Final Office Action issued by the United States Patent and Trademark Office for corresponding U.S. Appl. No. 16/030,605, dated Oct. 28, 2019.
Protest Under 37 C.F.R. 1.291(a) against Reissue U.S. Appl. No. 16/843,272, Jul. 17, 2020, 14 pages.
Protest Under 37 C.F.R. 1.291(a) against Reissue U.S. Appl. No. 16/854,395, Jul. 17, 2020, 14 pages.
Protest Under 37 C.F.R. 1.291(a) against Reissue U.S. Appl. No. 16/854,406, Jul. 17, 2020, 14 pages.
Protest Under 37 C.F.R. 1.291(a) against Reissue U.S. Appl. No. 16/842,389, Jul. 28, 2020, 20 pages.
Stipulation of Dismissal 2:17-cv-12358, Jun. 12, 2020, 1 page.
Letter to Judge Cecchi of NJ District Court regarding reissue office actions and protests filed in NJ District Court, Jul. 30, 2020, 3 pages.
Maleczka, R. E., Supplemental Declaration of Robert E. Maleczka, Jr., Ph.D., IPR2018-01766, Exhibit 2006, 9 pages, dated May 7, 2019.
Protest Under 37 C.F.R. 1.291(a) against Reissue U.S. Appl. No. 16/863,384, dated Aug. 3, 2020, 26 pages.
Notice of Allowance, Reissue U.S. Appl. No. 16/843,272, dated Aug. 25, 2020, 12 pages.
Notice of Allowance, Reissue U.S. Appl. No. 16/854,406, dated Aug. 26, 2020, 12 pages.
Liu Fuming Process Design of the Ammonolysis Reaction of Taurine, China Chemical Trade, 2013, No. 8, pp. 120. (Original article is published in China in Chinese, an English translation by the Applicant is included).
Liu Fuming, Xie Liming Study on the Ammonolysis Reaction For Taurine, Shandong Chemical Industry, 2015, 44 (5), p. 27-28,30. (Origianl article is published in Chinese. An English translation by the Applicant is included).
International Search Report for corresponding International Application No. PCT/CN2015/000232, dated Jul. 1, 2015.
Extended European Search Report and the European Search Opinion completed Apr. 5, 2017 for corresponding European Application No. 17157022.9.
USPTO Non-Final Office Action for corresponding U.S. Appl. No. 15/228,568 dated Oct. 5, 2016.
USPTO Non-Final Office Action for corresponding U.S. Appl. No. 14/120,651 dated Mar. 15, 2016.
International Search Report and Written Opinion for corresponding International Application No. PCT/US2017/018527, dated Jun. 8, 2017.
Japanese Notice of Reasons for Rejection, dated Jun. 13, 2017 with English machine translation, for corresponding Japan application No. 2017-033759.
USPTO Non-Final Office Action for corresponding U.S. Appl. No. 15/228,539 dated Oct. 17, 2016.
USPTO Non-Final Office Action for corresponding U.S. Appl. No. 14/120,046 dated Aug. 26, 2015.
Canadian First Office Action, dated Nov. 2, 2017 for corresponding Canada Application No. 2,946,181.
*Hubei Grand Life Science and Technology Co., Ltd* v. *Vitaworks IP, LLC*, Case No. IPR2018-01766, Petition for Inter Parte Review of U.S. Pat. No. 9,428,450 Under 37 C.F.R. § 42.100, Sep. 28, 2018, pp. 80 Alexandria, Virginia.
*Hubei Grand Life Science and Technology Co., Ltd* v. *Vitaworks IP, LLC*, Case No. IPR2018-01767, Petition for Inter Parte Review of U.S. Pat. No. 9,428,451 Under 37 C.F.R. § 42.100, Sep. 28, 2018, pp. 88, Alexandria, Virginia.
*Hubei Grand Life Science and Technology Co., Ltd* v. *Vitaworks IP, LLC*, Case No. IPR2018-01768 Petition for Inter Parte Review of U.S. Pat. No. 9,573,890 Under 37 C.F.R. § 42.100, Sep. 28, 2018, pp. 82, Alexandria, Virginia.
Declaration of Mark A. Lipton in Support of Petition for Inter Partes Review of U.S. Pat. No. 9,428,450 Under 37 C.F.R. § 42.100, Sep. 28, 2018, pp. 65.
Declaration of Mark A. Lipton in Support of Petition for Inter Partes Review of U.S. Pat. No. 9,428,451 Under 37 C.F.R. § 42.100, Sep. 28, 2018, pp. 69.
Declaration of Mark A. Lipton in Support of Petition for Inter Partes Review of U.S. Pat. No. 9,573,890 Under 37 C.F.R. § 42.100, Sep. 28, 2018, pp. 66.
Bondavera et al., Pharmaceutical Chemistry Journal, Synthesis of Taurine, Mar. 2008, pp. 142-144, vol. 42, No. 3, Springer Science+ Business Media, Inc, Secaucus, New Jersey.
Liu Fuming, China Chemical Trade, Process Design of Taurine, Year 2013, p. 120, vol. 5, No. 6, China National Chemical Center, Beijing City, China http://chemmedia.com.cn/GotoBin/Select.DLL.
Journal of Hubei Institute of Technology, Opimization on Ammonolysis in Manufacturing Method of Taurine,Year 2004, pp. 23-26, vol. 19, No. 1, Sum No. 66, Editorial Department of Journal of Hubei Polytechnic University, Wuhan, China.
Patent Owner's Preliminary Response for Inter Partes Review of U.S. Pat. No. 9,428,450 IPR2018-01766, dated Jan. 11, 2019, 50 pages.
Patent Owner's Preliminary Response for Inter Partes Review of U.S. Pat. No. 9,428,451 IPR2018-01767, dated Jan. 14, 2019, 62 pages.
Patent Owner's Preliminary Response for Inter Partes Review of U.S. Pat. No. 9,573,890 IPR2018-01768, dated Jan. 16, 2019, 54 pages.
Robert E. Maleczka's Declaration In Support of Patent Owner's Preliminary Response for Inter Partes Review of U.S. Pat. No. 9,428,450 IPR2018-01766, dated Jan. 11, 2019, 60 pages.
Robert E. Maleczka's Declaration In Support of Patent Owner's Preliminary Response for Inter Partes Review of U.S. Pat. No. 9,428,451 IPR2018-01767, dated Jan. 14, 2019, 75 pages.
Robert E. Maleczka's Declaration In Support of Patent Owner's Preliminary Response for Inter Partes Review of U.S. Pat. No. 9,573,890 IPR2018-01768, dated Jan. 16, 2019, 67 pages.
Decision re Institution of Inter Partes Review issued for Case IPR2018-01766 for corresponding U.S. Pat. No. 9,428,450, dated Apr. 9, 2019, 45 pages.
Decision re Institution of Inter Partes Review issued for Case IPR2018-01767 for corresponding U.S. Pat. No. 9,428,451, dated Apr. 10, 2019, 25 pages.
Decision re Institution of Inter Partes Review issued for Case IPR2018-01768 for corresponding U.S. Pat. No. 9,573,890, dated Apr. 10, 2019, 23 pages.
Patent Owner's Response for Inter Partes Review of U.S. Pat. No. 9,428,450 IPR2018-01766, dated Jul. 12, 2019, 66 pages.

* cited by examiner

Fig. 1. Schematic Flowchart for the Cyclic Production of Taurine
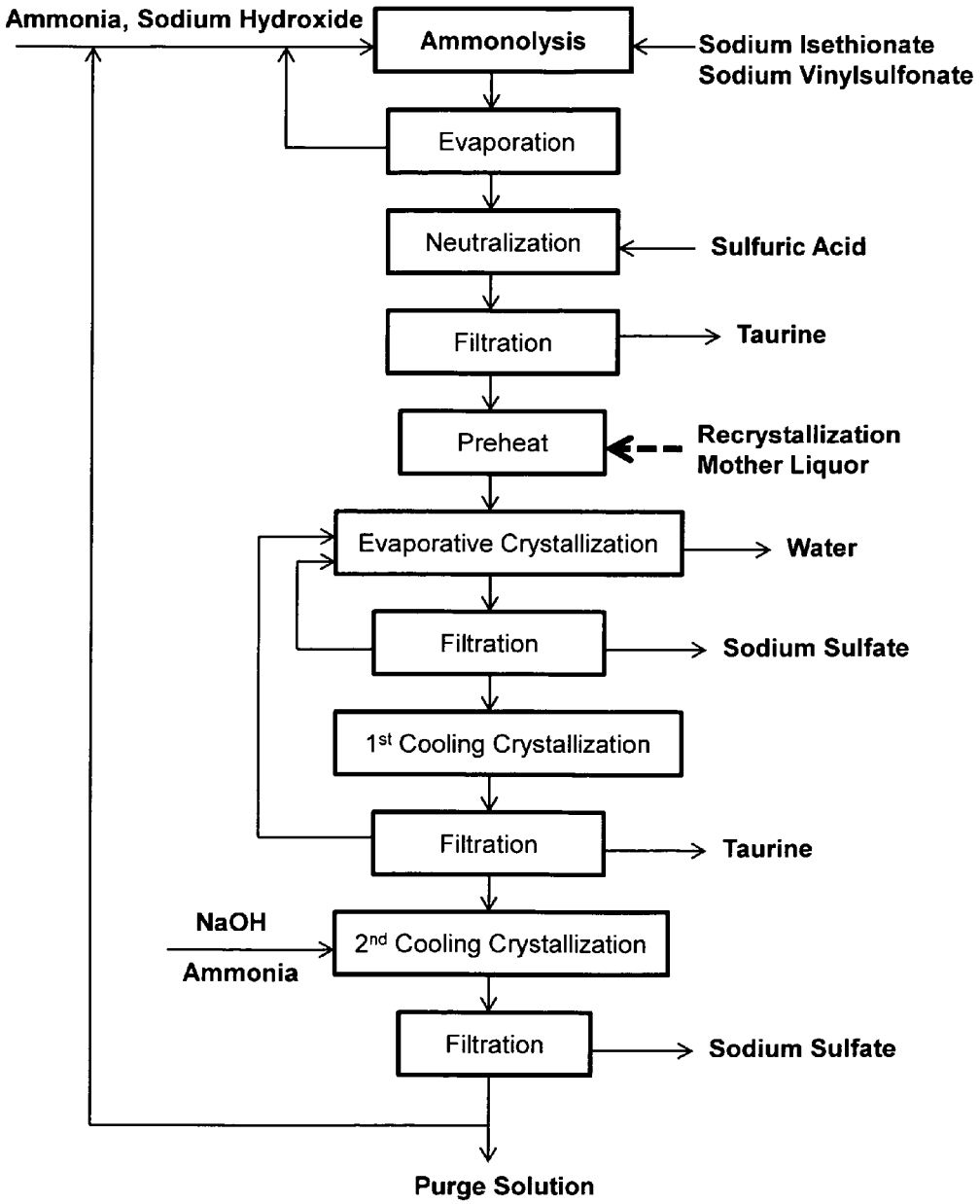

Fig. 2. Solubility Curve of Taurine and Sodium Sulfate in Water
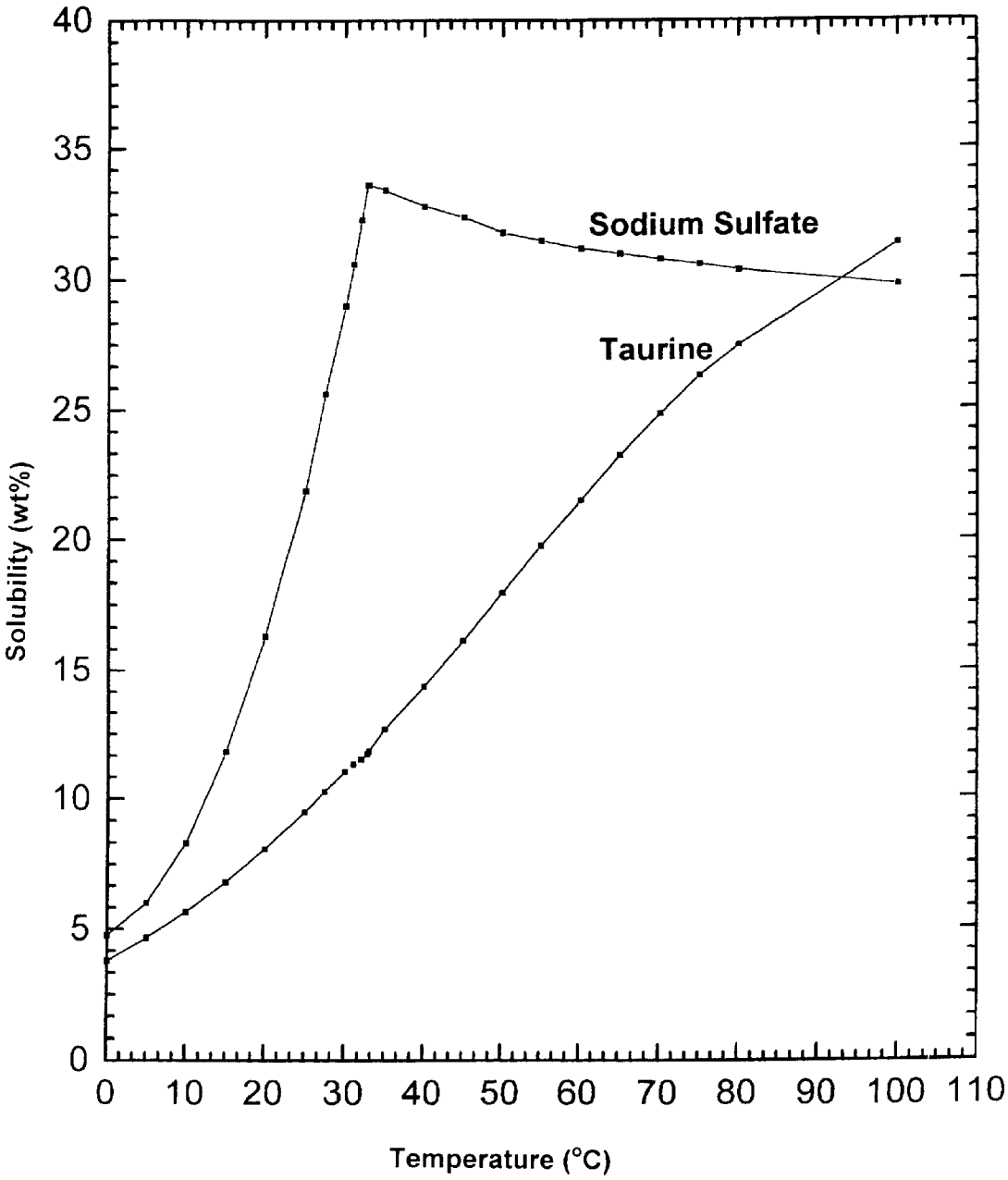

CYCLIC PROCESS FOR THE PRODUCTION OF TAURINE FROM ALKALI ISETHIONATE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a continuation-in-part of [co-pending application] *U.S.* Ser. No. 14/120,046, filed on Apr. 18, 2014*, now U.S. Pat. No. 9,428,450, issued on Aug. 30, 2016.*

TECHNICAL FIELD

The present invention relates to a cyclic process for the production of taurine from alkali isethionate and from alkali vinyl sulfonate in a high overall yield, i.e., greater than 90%, in particular, greater than 95%, by continuously converting the byproducts of the ammonolysis reaction, alkali ditaurinate and alkali tritaurinate, to alkali taurinate.

BACKGROUND OF THE INVENTION

Taurine can be referred to as 2-aminoethanesulfonic acid and is one of the amino sulfonic acids found in the tissues of many animals. Taurine is an extremely useful compound because it has such pharmacological effects as detoxification effect, fatigue-relieving effect and nourishing and tonifying effect. As a result, taurine finds wide applications as an essential ingredient for human and animal nutrition.

Taurine is currently produced in an amount of over 50,000 tons per year from ethylene oxide and monoethanolamine. At present time, most of the taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large amount of waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate.

According to the co-pending application U.S. Ser. Nos. 13/999,203 and 13/999,439, these same issues are also encountered in the production of taurine from ethanol and ethylene, respectively. Sodium isethionate is a key common intermediate and the ammonolysis of sodium isethionate is an important step in the ethanol and ethylene processes.

U.S. Pat. No. 1,932,907 discloses that sodium taurinate is obtained in a yield of 80%, when sodium isethionate undergoes ammonolysis reaction in a molar ratio of 1:6.8 for 2 hrs at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD 219 023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di-and tri-taurinate.

WO 01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

From these prior arts, it is therefore concluded that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins, first strongly acid ion exchange resin in hydrogen form, and then an anion exchange resin in basic form. This process is complicated and requires the use of large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities. It is desirable to have available a process for further separation of these components to achieve an economical process and to reduce the amount of waste stream.

It is, therefore, an object of the present invention to disclose a cyclic process for the production of taurine from alkali isethionate and from alkali vinyl sulfonate in a high overall yield, i.e., greater than 90%, in particular, greater than 95%. According to the process in the present invention, sodium ditaurinate and sodium tritaurinate, byproducts from the ammonolysis of sodium isethionate or sodium vinyl sulfonate, are continuously converted to sodium taurinate in the ammonolysis stage.

It is another object of the present invention to disclose a process for the preparation of pure sodium ditaurinate and pure sodium tritaurinate, and their conversion to sodium taurinate. When sodium ditaurinate and sodium tritaurinate are reacted with aqueous ammonia under ammonolysis reaction conditions, a mixture of similar compositions of sodium taurinate, ditaurinate, and tritaurinate is formed in an equilibrium state. This novel finding renders the cyclic process possible.

It is a further object of the present invention to disclose a process for the effective separation of sodium sulfate from residual taurine, byproducts, i.e., sodium ditaurinate and sodium tritaurinate, and unreacted starting material, i.e., sodium isethionate. According to the process in the present invention, the residual taurine, which is less soluble, is converted to a highly soluble form, i.e., sodium taurinate or ammonium taurinate, to facilitate the cooling crystallization of sodium sulfate. The mother liquor, consisting of sodium taurinate, sodium ditaurinate, sodium tritaurinate, and sodium isethionate, is recycled to the ammonolysis reaction to produce sodium taurinate.

DESCRIPTION OF THE DRAWINGS

FIG. 1. Schematic flowchart for the cyclic production of taurine from sodium isethionate and sodium vinyl sulfate.

FIG. 2. Solubility curves for taurine and sodium sulfate in water.

DESCRIPTION OF THE INVENTION

The present invention relates to a cyclic process for the production of taurine from alkali isethionate, which is a key intermediate for the ethylene oxide, ethanol, and ethylene processes. This cyclic process is also applied to the production of taurine from alkali vinyl sulfonate, another intermediate for the ethanol and ethylene processes.

For the production of taurine, sodium isethionate and sodium vinyl sulfonate are preferably used, but other alkali metals, i.e., lithium, potassium, and cesium, are equally suitable. In the drawings and following description, only sodium is used in replace of alkali metals to describe the process.

In order to achieve the cyclic process, the present invention discloses a novel finding and process for converting sodium ditaurinate and sodium tritaurinate, identified as byproducts of the ammonolysis reaction of sodium isethionate, to sodium taurinate under the ammonolysis conditions. According to the cyclic process in the present invention, sodium isethionate and sodium vinyl sulfonate are converted to sodium taurinate in a practically quantitative yield. A highly effective process for the separation of sodium sulfate from taurine and other byproducts is developed to ensure that taurine is obtained in high yield, i.e., greater than 90%, in particular greater than 95%, on the basis of sodium isethionate or sodium vinyl sulfonate.

Although sodium ditaurinate and sodium tritaurinate are mentioned in the prior arts, preparation of pure products is not known. The present invention describes a method for the preparation of pure sodium ditaurinate and pure sodium tritaurinate from diethanolamine and triethanolamine, respectively.

To prepare sodium ditaurinate, diethanolamine is first reacted with excess thionyl chloride to form bis(2-chloroethyl)amine hydrochloride in quantitative yield, which undergoes sulfonation with sodium sulfite to yield the expected product. When triethanolamine is used in the same sequence of reactions, tris(2-chloroethyl)amine hydrochloride is obtained as an intermediate, disodium tritaurinate is obtained as an aqueous solution, along with sodium chloride. The reaction schemes are as follows:

$$HN(CH_2CH_2OH)_2 + 2SOCl_2 \longrightarrow HN(CH_2CH_2Cl)_2 \xrightarrow{Na_2SO_3} HN(CH_2CH_2SO_3H)(CH_2CH_2SO_3Na)$$

Sodium Ditaurinate

-continued $$N(CH_2CH_2OH)_3 + 3SOCl_2 \longrightarrow N(CH_2CH_2Cl)_3 \xrightarrow{Na_2SO_3} N(CH_2CH_2SO_3H)(CH_2CH_2SO_3Na)_2$$

Sodium Tritaurinate

When sodium ditaurinate and sodium tritaurinate are subjected to the ammonolysis reaction in aqueous ammonia under the same conditions at a temperature of 220° C. for 2 hours, a mixture of similar compositions, i.e., sodium taurinate (74%), sodium ditaurinate (23%), and sodium tritaurinate (3%), is obtained. Clearly, an equilibrium state is reached among the three taurinates, irrespective of the starting materials.

This novel finding renders possible the cyclic process for preparing taurine from sodium isethionate and from sodium vinyl sulfonate, because the inevitable byproducts of the ammonolysis step, i.e., sodium ditaurinate and sodium tritaurinate, can be continuously converted to sodium taurinate in each successive cycle.

FIG. 1 describes the detailed unit operations for the cyclic process for the production and isolation of taurine from sodium isethionate. The cycle is equally applicable for the production of taurine from sodium vinyl sulfonate.

The cyclic process starts from the ammonolysis of sodium isethionate or sodium vinyl sulfonate in aqueous ammonia at a temperature of 180 to 270° C. under a pressure from the autogenous to 260 bars, and optionally, in the presence of catalysts. Usually, catalysts are the alkaline salts of sodium, potassium and lithium. Such salts are sodium hydroxide, potassium hydroxide, lithium hydroxide, sodium carbonate, potassium carbonate, lithium carbonate, sodium sulfate, sodium sulfite, potassium sulfate, potassium sulfite. Any one or a combination of two or more these salts can be used as catalyst to influence the reaction.

After the ammonolysis reaction, the excess ammonia are dispelled from the reaction solution and reclaimed for reuse. Sodium taurinate is obtained, along with sodium ditaurinate, sodium tritaurinate, and unreacted sodium isethionate.

The strongly basic solution is neutralized with sulfuric acid to pH 5-7 to yield mainly taurine, sodium sulfate, sodium ditaurinate, and sodium tritaurinate. The content of taurine and sodium sulfate is in a molar ratio of 1:0.5 to 1:0.6, and nearly the same in terms of their weight.

The initial solution is optionally concentrated, then cooled to 28 to 35° C., to crystallize taurine. The first batch of crude taurine is obtained by filtration, while sodium sulfate remains in solution. Lower temperature is to be avoided to prevent the crystallization of sodium sulfate.

It is important to point out that sodium sulfate has the maximum solubility at a temperature of 33° C. as shown in FIG. 2. The solubility of sodium sulfate decreases slightly from 33 to 100° C., but drastically from 33 to 0° C. Moreover, sodium sulfate crystallizes as anhydrous form above 40° C., but as Glauber's salt, i.e., sodium sulfate decahydrate at a temperature below 30° C.

The mother liquor is now consisted of about 30% of sodium sulfate and about 10% of taurine, along with various percentages of sodium ditaurinate and sodium tritaurinate. This solution is concentrated to about one half to one third of its original volume in an evaporative crystallizer, at a temperature from 70 to 95° C., preferably 75 to 85° C., to yield a suspension of sodium sulfate, which is removed by filtration at the same temperature. The temperature is kept high enough to prevent the crystallization of taurine at this stage.

The filtration mother liquor, now saturated with sodium sulfate and rich in taurine, is cooled to 33-35° C. in the 1st cooling crystallizer to crystallize the second crop of crude taurine.

The cycle of evaporative crystallization at higher temperature, preferably from 75 to 85° C., to remove sodium sulfate, and the first cooling crystallization at lower temperature, preferably at 33-35° C., can be continued until the solid content of impurities, mainly sodium ditaurinate and sodium tritaurinate, accumulates to about 30% of the solid content in the mother liquor.

The mother liquor from the first cooling crystallization stage after separating taurine is usually comprised of 25-30% of sodium ditaurinate and tritaurinate, 8-9% of taurine, and 30-35% of sodium sulfate.

If the mother liquor from the first cooling crystallization stage is cooled to 10 to 15° C., taurine and sodium sulfate decahydrate, i.e., Glauber's salt will co-crystallize at the same time. This is clearly demonstrated in FIG. 2 of the solubility curve of sodium sulfate and taurine in the region of 0° C. to 33° C. The mixture of taurine and Glauber's salt requires further dissolution and separation in the preheating and dissolution unit.

Although the solubility of sodium sulfate and taurine shows the same decreasing trend as the temperature is lowered from 33° C. to 0° C., it has now been found that the solubility of taurine can be drastically increased by converting taurine to ammonium taurinate or sodium taurinate. This is achieved by adjusting the pH of the mother liquor from 5-6 to a pH of 10-12 by adding an aqueous solution of ammonia or sodium hydroxide, preferably sodium hydroxide. The solubility of sodium taurinate is found to be more than 90 g/100 g in water from 0° C. to 30° C. Taurine is soluble to 36 g in 100 g of 25% aqueous ammonia at room temperature.

It is also found that the solubility of sodium sulfate can be further decreased by saturating aqueous solution of sodium sulfate with ammonia. It is thus possible to effectively separate sodium sulfate from residual taurine by simply adjusting the pH of the mother liquor and, optionally, saturating the mother liquor with ammonia. Upon cooling in the 2nd cooling crystallizer, only sodium sulfate is precipitated from the mother liquor and removed by filtration.

If ammonia or ammonium hydroxide is used to adjust the pH, the mother liquor after removal of sodium sulfate needs to be fortified with sodium hydroxide to facilitate the ammonolysis of ditaurinate and tritaurinate to taurinate. The amount of sodium hydroxide used is from 2 to 30% of the amount of total taurinates.

The mother liquor from the 2nd cooling crystallization stage after separating sodium sulfate is usually comprised of 25-30% of sodium ditaurinate and tritaurinate, 8-9% of sodium taurinate, and 5-8% of sodium sulfate. This solution is then saturated with ammonia to 15 to 28% and returned to the ammonolysis step. Optionally, this solution may be combined with a new batch of sodium isethionate or sodium vinyl sulfonate for the ammonolysis step.

Some of the mother liquor from the 2nd cooling crystallization needs to be purged from the production cycle, when uncharacterized impurities start to adversely influence the quality of the product. The amount of purge solution in each cycle depends on the quality of starting materials, in particular, sodium isethionate and sodium vinyl sulfonate. If crude sodium isethionate in the ethylene oxide process is used, purge is required in an amount from 2 to 25% in terms of the volume of the mother liquor, because ethylene glycol, a byproduct from the reaction of ethylene oxide with water, starts to accumulate. If pure sodium isethionate or sodium isethionate prepared from ethanol and ethylene is used, no purge is necessary at all.

Crude taurine obtained in the cyclic process is recrystallized from deionized water one or more times to yield a product of pharmaceutical grade. The recrystallization mother liquor may be reused several times until it affects the quality of the product obtained. This mother liquor, consisting of residual taurine, sodium sulfate, and impurities, is then sent to a preheat unit for the evaporative crystallization and further treatment.

It should be appreciated that no waste is generated in the cyclic process according to the present invention for the production of taurine from ethanol and ethylene, because sodium sulfate, discharged in the cyclic process, is recycled continuously to prepare sodium isethionate and sodium vinyl sulfonate.

The process according to the present invention can be carried out discontinuously, semi-continuously, and continuously.

EXAMPLES

The following examples will illustrate the practice of this invention but are not intended to limit its scope.

Example 1

This example relates to the preparation of sodium ditaurinate and its reaction with aqueous ammonia under ammonolysis reaction conditions.

Into a 1 L flask, equipped a refluxing condenser, is added 31.5 g (0.30 mole) of diethanolamine and 300 mL of dichloroethane, then 51.0 mL of thionyl chloride. Solid suspension formed immediately after the addition of thionyl chloride and then dissolved upon warming to 50° C. During refluxing, the solid suspension is dissolved and then the crystalline solid appears. The crystalline suspension is refluxed while being stirred for 3 hrs. The reaction is quenched by adding 20 mL of methanol and the solvents are removed under vacuum. A white crystalline material, bis(2-chloroethyl)amine hydrochloride, weighted 53.0 g, is obtained in a quantitative yield.

To the flask is added 500 mL of deionized water, 100 g of sodium sulfite. The solution is stirred at a temperature first at 50-60° C. for 3 hrs, then at 95° C. for 4 hrs. HPLC and LC-MS shows complete conversion of the starting material to the desired sodium ditaurinate.

The excess sodium sulfite is destroyed by addition of 40 mL of 30% hydrochloric acid, followed by careful adjustment of pH to 6-7 with sodium carbonate. The solution consists of practically pure sodium ditaurinate and sodium chloride. The solution may be used directly in the ammonolysis reaction.

To obtain pure sodium ditaurinate, the aqueous solution is vacuum dried to give a white solid. Into the flask is added 600 mL of anhydrous methanol, and the suspension is refluxed for 30 minutes to dissolve sodium ditaurinate in methanol. After filtration to remove sodium chloride, the methanol solution is cooled to room temperature to crystallize pure sodium ditaurinate, which is used as analytical standard.

Crude sodium ditaurinate, prepared from 0.30 mole of diethanolamine, is dissolved in 300 mL of water containing 26.0 g of sodium hydroxide. The solution is then mixed with 600 mL of 25% aqueous ammonia and heated in an autoclave at 220° C. for 2 hrs.

HPLC analysis of the reaction solution shows the formation of sodium taurinate (74%), sodium ditaurinate (24%), and sodium tritaurinate (2%) on the molar basis.

Example 2

This example relates to the preparation of sodium tritaurinate and its reaction with aqueous ammonia under ammonolysis reaction conditions.

Into a 1 L flask, equipped with a refluxing condenser, is added 29.8 g (0.20 mole) of triethanolamine, 300 mL of dichloroethane, then 51.0 mL of thionyl chloride. The mixture is heated to reflux for 4 hrs. The reaction is quenched by adding 20 mL of methanol. Removal of solvent gives a white crystalline mass of tris(2-chloroethylamine) hydrochloride in quantitative yield.

To the flask is added 500 mL of deionized water, 100 g of sodium sulfite. An oil phase is separated first. After heating at 60° C. for 2 hrs and 98° C. for 5 hrs, the oil phase disappears and a clear solution is obtained. HPLC and LC-MS shows complete conversion of the starting material to the desired sodium tritaurinate.

The crude reaction solution is transferred to a 2 L autoclave, to which 26 g of sodium hydroxide and 600 mL of 25% aqueous ammonia are added. The autoclave is heated to 220° C. for 2 hrs to carry out the ammonolysis reaction.

HPLC and LC-MS analysis shows that sodium tritaurinate is converted to a mixture of sodium taurinate (72%), sodium ditaurinate (23%), and sodium tritaurinate (5%) on the molar basis.

Example 3

This example demonstrates the conversion of sodium ditaurinate and sodium tritaurinate in the recrystallization mother liquor to sodium taurinate.

To 200 mL of the mother liquor from $2^{nd}$ cooling crystallization stage, composed of sodium ditaurinate (25% by wt), sodium tritaurinate (3% by wt), taurine (5% by wt), and sodium sulfate (6% by wt), is added 15 g of sodium hydroxide, 500 mL of 25% aqueous ammonia. The solution is heated in a 2 L autoclave at 220° C. for 2 hrs to carry out the ammonolysis reaction.

HPLC and LC-MS analysis shows that the reaction solution is comprised of the following taurinates: sodium taurinate (76%), sodium ditaurinate (21%), and sodium tritaurinate (3%) on the molar basis.

Example 4

This example is directed to a process for the separation of sodium sulfate from sodium taurinate, sodium ditaurinate, and sodium tritaurinate.

A starting solution is prepared by first boiling the solution from the ammonolysis reaction to remove excess ammonia, and then adding enough sulfuric acid to pH 5-7. The solution is consisted of 30% taurine, 26% sodium sulfate, and 7% sodium di-and tri-taurinates.

2000 g of the starting solution is cooled from 80° C. to 33° C. to form a slurry consisting essentially of the first crop of crystallized taurine, which is separated by filtration at 33° C. and washed with 100 g of cold water. The recovered taurine is dried and weighed 398 g.

The separated mother liquor, weighed 1580 g, is boiled to evaporate to 900 g to form a slurry of sodium sulfate. This slurry is cooled to 80° C. and filtered to recover sodium sulfate, weighed 304 g.

The mother liquor, containing 202 g of taurine and 216 g of sodium sulfate, is cooled to 33° C. to form second slurry of taurine. After filtration and washing with cold water, 124 g of taurine is obtained.

The mother liquor from the previous step, now containing 78 of taurine and 216 g of sodium sulfate, is added a solution of sodium hydroxide to pH 11, saturated with ammonia, and cooled to 10° C. in 2 hours to obtain a slurry of sodium sulfate, which is removed by filtration.

This final mother liquor, about 500 g, is consisted of sodium ditaurinate and tritaurinate (28%, 140 g), sodium taurinate (78 g, 15%), and sodium sulfate (35 g, 7%). This solution is used for the ammonolysis reaction.

It will be understood that the foregoing examples, explanation, drawings are for illustrative purposes only and that in view of the instant disclosure various modifications of the present invention will be self-evident to those skilled in the art and are to be included within the spirit and purview of this application and the scope of the appended claims.

What is claimed is:

[1. A cyclic process for the production of taurine from alkali isethionate, comprising, (a) adding an excess of ammonia to a solution of alkali isethionate and subjecting the solution to ammonolysis reaction in the presence of one or more catalysts to yield a mixture of alkali taurinate, alkali ditaurinate, alkali tritaurinate, and unreacted alkali isethionate;

(b) recovering the excess ammonia from (a) and neutralizing the solution with sulfuric acid to obtain a crystalline suspension of taurine in a solution of alkali sulfate, alkali ditaurinate, alkali tritaurinate, and alkali isethionate;

(c) separating taurine from (b) to provide a mother liquor (d) adjusting the pH of the mother liquor to basic to convert taurine present in the mother liquor to alkali taurinate and prevent the crystallization of taurine, and removing alkali sulfate from the mother liquor by performing evaporative crystallization and cooling crystallization through solid-liquid separation;

(e) returning the mother liquor of (d) to (a) for further ammonolysis of alkali ditaurinate, alkali tritaurinate, and unreacted alkali isethionate.]

[2. The process according to claim 1, wherein the mother liquor containing alkali ditaurinate, and alkali tritaurinate is mixed with a new batch of alkali isethionate to inhibit the formation of alkali ditaurinate and alkali tritaurinate and to convert alkali ditaurinate and alkali tritaurinate to alkali taurinate during the ammonolysis.]

[3. The process according to claim 2, wherein alkali ditaurinate and alkali tritaurinate in the returning mother liquor are converted to di-alkali ditaurinate and tri-alkali tritaurinate by adding alkali hydroxide during the ammonolysis.]

[4. The process according to claim 1, wherein the one or more catalysts for the ammonolysis are comprised of sodium hydroxide, potassium hydroxide, lithium hydroxide, sodium carbonate, potassium carbonate, lithium carbonate, sodium sulfate, sodium sulfite, potassium sulfate, or potassium sulfite.]

[5. The process according to claim 1, wherein the overall yield is greater than 85%.]

[6. The process according to claim 1, wherein the overall yield is greater than 90%.]

[7. The process according to claim 1, wherein the overall yield is greater than 95%, to nearly quantitative.]

[8. The process according to claim 1, wherein alkali metals are lithium, sodium, and potassium.]

*9. A cyclic process for the production of taurine from alkali isethionate in an overall molar yield of at least 85% on the basis of alkali isethionate, comprising,*

(*a*) *adding excess ammonia to a solution comprised of alkali isethionate and subjecting the solution to ammonolysis in the presence of at least one catalyst to yield a mixture of alkali taurinate, dialkali ditaurinate, trialkali tritaurinate, and unreacted alkali isethionate;*

(*b*) *removing excess ammonia from the solution of step* (*a*) *and neutralizing the solution with sulfuric acid to form a crystalline suspension of taurine in a solution comprised of alkali sulfate, alkali ditaurinate, alkali tritaurinate, and unreacted alkali isethionate;*

(*c*) *recovering taurine by means of solid-liquid separation to obtain a mother liquor solution comprised of alkali ditaurinate, alkali tritaurinate, unreacted alkali isethionate, and unrecovered taurine;*

(*d*) *adjusting the pH of the mother liquor solution to basic with an alkali hydroxide wherein the molar amount of the alkali hydroxide is at least equal to the molar amount of the total taurinates in the mother liquor solution comprised of the alkali ditaurinate and alkali tritaurinate, so as to convert the taurine in the mother liquor solution to alkali taurinate and prevent the crystallization of taurine, and removing the alkali sulfate from the mother liquor solution by performing evaporative and cooling crystallization by means of solid-liquid separation; and*

(*e*) *returning the mother liquor solution of step* (*d*) *to step* (*a*) *and performing steps* (*a*), (*b*), (*c*), *and* (*d*).

*10. The process according to claim 9, wherein the mother liquor solution of the step* (*d*) *is mixed with a new batch of alkali isethionate.*

*11. The process according to claim 9, wherein the catalyst for the ammonolysis is selected from the group consisting of sodium hydroxide, potassium hydroxide, lithium hydroxide, sodium carbonate, potassium carbonate, lithium carbonate, sodium sulfate, sodium sulfite, potassium sulfate, and potassium sulfite.*

*12. The process according to claim 9, wherein the overall molar yield of the taurine from the alkali isethionate is greater than 85%.*

*13. The process according to claim 9, wherein the overall molar yield of the taurine from the alkali isethionate is greater than 90%.*

*14. The process according to claim 9, wherein the overall molar yield of the taurine from the alkali isethionate is greater than 95%, to nearly quantitative.*

*15. The process according to claim 9, wherein the alkali is lithium, sodium, or potassium.*

* * * * *